United States Patent
Herz et al.

(10) Patent No.: US 7,192,714 B2
(45) Date of Patent: Mar. 20, 2007

(54) LDL RECEPTOR SIGNALING ASSAYS

(75) Inventors: Joachim Herz, Dallas, TX (US); Petra May, Dallas, TX (US)

(73) Assignee: Board of Regents, The University of Texas System, Austin, TX (US)

( * ) Notice: Subject to any disclaimer, the term of this patent is extended or adjusted under 35 U.S.C. 154(b) by 756 days.

(21) Appl. No.: 09/977,155

(22) Filed: Oct. 12, 2001

(65) Prior Publication Data

US 2003/0077672 A1    Apr. 24, 2003

(51) Int. Cl.
*G01N 33/53*    (2006.01)

(52) U.S. Cl. .................. 435/7.1; 435/69.6; 514/2; 514/4; 530/300; 530/301; 530/324; 530/350

(58) Field of Classification Search ............. 435/7.1, 435/69.6; 514/2, 4; 530/300, 301, 324, 530/350
See application file for complete search history.

(56) References Cited

OTHER PUBLICATIONS

Kinoshita et al. "Denonstration by FRET of two sites interaction between LDL-receptor related protein and the amyloid precursor protein: role of the intracellular adapter protein Fe65." The Journal of Neuroscience, Nov. 1, 2001, 21(21):8354-8361. Reprint 1-20.*
Herz "The LDL receptor gene family: Unexpected signal transducers in the brain." Neuron, vol. 29, Mar. 2001, pp. 571-581.*
Weiss, "Hypursuite: A Hierarchical Network Search Engine that Exploits Content-Link Hypertext Clustering," Hypertext '96, Mar. 16-20, 1996, pp. 180-193.
Chen, "Bringing Order to the Web: Automatically Categorizing Search Results," CHI '2000 Conference Proceedings, Apr. 1-May 2000, pp. 145-152.
Dumais, "Hierarchical Classification of Web Content," SIGIR 2000, Jul. 24-28, 2000; vol. 34, pp. 256-263.
Kim et al., Biochimica et Biophysica Acta. 1518:204-209, Mar. 19, 2001.
Horn et al. Journal of Biological Chemistry 272(21):13608-13613, May 23, 1997.
Hua et al. Journal of Biological Chemistry 271(17):10379-10384, Apr. 26, 1996.
Willnow et al. Journal of Biological Chemistry 269(22):15827-15832, Jun. 3, 1994.
Sanchez et al. Archive of Biochemistry and Biophysica 389(2):218-22, May 16, 2001.
May et al. Journal of Biological Chemistry 277(21):18736-18743, May 24, 2002.

* cited by examiner

*Primary Examiner*—Long V. Le
*Assistant Examiner*—Lisa V. Cook
(74) *Attorney, Agent, or Firm*—Richard Aron Osman

(57) ABSTRACT

The invention provides methods and compositions for modeling and detecting LDL receptor transmembrane signaling by detecting proteolysis of an LDL receptor transmembrane domain. The method comprises the steps of: a) providing a sample comprising a cell membrane comprising (i) a polypeptide comprising an LDL receptor transmembrane domain fused to a C-terminal tail, and (ii) a protease which specifically cleaves the domain and thereby releases the tail from the membrane; b) incubating the sample under conditions wherein the protease cleaves the domain and thereby releases the tail from the membrane; and c) detecting a resultant released tail.

20 Claims, No Drawings

LDL RECEPTOR SIGNALING ASSAYS

The work carried out in the subject application was supported in part by grants from the National Institutes of Health (HL20948 and HL63762). The government may have rights in any patent issuing on this application.

INTRODUCTION

Field of the Invention

The field of this invention is LDL receptor signaling assays.

BACKGROUND OF THE INVENTION

The members of the low density lipoprotein (LDL) receptor gene family bind a broad spectrum of extracellular ligands. Traditionally, they had been regarded as mere cargo receptors that promote the endocytosis and lysosomal delivery of these ligands. However, recent genetic experiments have revealed critical functions for LDL receptor family members in the transmission of extracellular signals and the activation of intracellular tyrosine kinases. This process regulates neuronal migration and is crucial for brain development. Signaling through these receptors has been reported to require the interaction of their cytoplasmic tails with a number of intracellular adaptor proteins, including Disabled-1 (Dab1) and FE65. See copending U.S. Ser. No. 09/562,737.

We have now discovered that members of the LDL receptor gene family undergo endoproteolytic processing events that result in the release of their cytoplasmic tails into the cytoplasm. The present invention exploits this mechanism in novel methods and compositions for detecting proteolysis of LDL receptor transmembrane domains and resultant release of C-terminal tail domains.

Relevant Literature

Quinn et al. 1999, Exp Cell Res 251, 433–41; Grimsley et al., 1999, Thromb Res 94, 153–64; Herz, 2001, Neuron 29, 571–81; Van Uden et al. 1999, Mol Cell Neurosci 14, 129–140.

SUMMARY OF THE INVENTION

The invention provides methods and compositions for modeling and detecting LDL receptor transmembrane signaling by detecting proteolysis of an LDL receptor transmembrane domain. The method generally comprises the steps of: a) providing a sample comprising a cell membrane comprising (i) a polypeptide comprising an LDL receptor transmembrane domain fused to a C-terminal tail, and (ii) a protease which specifically cleaves the domain and thereby releases the tail from the membrane; b) incubating the sample under conditions wherein the protease cleaves the domain and thereby releases the tail from the membrane; and c) detecting a resultant released tail. Frequently, the sample further comprises a candidate agent which modulates the resultant cleavage and/or release, wherein an agent-biased cleavage and/or release is detected.

The invention provides numerous systems for practicing the method. For example, in one embodiment wherein the sample comprises a viable cell which comprises the membrane, the tail comprises an intracellular transcription factor domain, the cell further comprises a transcriptional reporter responsive to release of the transcription factor domain from the membrane, and the detecting step comprises detecting expression of the reporter as an indication of the released tail. In another embodiment the sample comprises a cellular membrane extract which comprises the membrane, and the detecting step comprises selectively detecting released, soluble tails, such as by solid-phase affinity adsorption assay. In preferred embodiments, the transmembrane domain is that of an LDL receptor selected from the group consisting of LRP, LRP1b, megalin, LDLR, VLDLR, ApoER2, MEGF7, LRP5, LRP6 and LR11, particularly LRP, LRP1b or megalin. The tail may comprise the native cytoplasmic domain of the LDL receptor or a truncation thereof, either of which may be fused to a transcription factor domain, an affinity tag, a label, etc. Alternatively, the tail may comprise an exclusively heterologous sequence. The recited protease is preferably native to the membrane, particularly gamma secretase. The subject compositions include systems and kits for the disclosed LDL receptor signaling assays.

DESCRIPTION OF PARTICULAR EMBODIMENTS OF THE INVENTION

The invention provides efficient methods of identifying agents, compounds or lead compounds for agents which modulate LDL receptor signaling, which is involved in a number of important pathologies, including Alzheimer disease and artherosclerosis. The methods are amenable to automated, cost-effective high throughput screening of chemical libraries for lead compounds. Identified reagents find use in the pharmaceutical industries for animal and human trials; for example, the reagents may be derivatized and rescreened in in vitro and in vivo assays to optimize activity and minimize toxicity for pharmaceutical development. The subject assays comprise the steps of: a) providing a sample comprising a cell membrane comprising (i) a polypeptide comprising an LDL receptor transmembrane domain fused to a C-terminal tail, and (ii) a protease which specifically cleaves the domain and thereby releases the tail from the membrane; b) incubating the sample under conditions wherein the protease cleaves the domain and thereby releases the tail from the membrane; and c) detecting a resultant released tail.

LDL receptors, as used herein, refers to the well-defined, structurally and functionally related LDL receptor gene family; see, Herz, 2001, Neuron 29, 571–81. The LDL receptors are all single span, transmembrane proteins that bind ApoE and comprise LDL receptor extracellular ligand binding-type repeats. To distinguish, the originally studied member of this genus, the LDL Receptor, or LDLR, will be referred to with a capital letter or by acronym. Preferred LDL receptors, core members, include LRP, LRP1b, megalin, LDLR, VLDLR, ApoER2, MEGF7, LRP5, LRP6 and LR11. Of particular interest are the highly related LRP, LRP1b and megalin proteins. These proteins are naturally found across diverse genera, including all animals, particularly mammals, and of particular interest for drug screens are the human versions. The recited LDL receptor comprises a naturally cleaved C-terminal, cytoplasmic tail, which is readily ascertained by confirming the presence of the cleaved tails in cells or extracts from cells either naturally expressing or overexpressing by transfection the intact or truncated LDL receptor. Such confirmation may involve one or more of the assays described herein, using a variety of cell types naturally expressing the receptor, each under a variety of assay conditions, as the receptors have varying cleavage propensities.

The recited transmembrane domain is well characterized across LDL receptors (see, Herz, 2001, Neuron 29, 571–81) and includes a specific cleavage site that effects release of the C-terminal cytoplasmic tail. This mechanism is analogous to that used by APP and Notch (see, e.g. Sastre et al., 2001, EMBO Reports 21(9), 835–41, esp. FIG. 4); hence, the assay protocols applicable to APP and Notch, are expressly applicable to the recited LDL receptors, including the variously described processing readout assays; see, e.g. Sastre, supra; Cao and Sudhof, Science Jul. 6, 2001 293 (5527):115–20, etc. In particular embodiments, the recited transmembrane domain is part of, or fused to, additional domains providing additional functionalities, including a dispatchable C-terminal domain (below) adapted to provide an assay readout, an N-terminal domain that modulates or provides additional ligand binding or activation functions, etc. For example, N-terminal domains of native or heterologous LDL receptors, or other heterologous ligand binding domains can be used to effect desired chimeric systems.

Accordingly, the invention provides numerous systems for practicing the method and obtaining a readout of LDL receptor proteolytic processing. For example, in one embodiment wherein the sample comprises a viable cell which comprises the membrane, the tail comprises an intracellular transcription factor domain, the cell further comprises a transcriptional reporter responsive to release of the transcription factor domain from the membrane, and the detecting step comprises detecting expression of the reporter as an indication of the released tail. A wide variety of transcriptional activator/reporter assays are known in the art, including Gal4 and LexA reporters. These transcription factor domains may activate the reporter directly, indirectly, or in concert with one or more additional transcription factor domains expressed in the cell. In a particular embodiment, native LDL receptor C-terminal residues may used as the transcription factor domain or transcription factor binding domain or docking site for a scaffold protein which promotes target gene transcription to modulate reporter expression.

In another embodiment wherein the sample comprises a cellular membrane extract which comprises the membrane, and the detecting step comprises selectively detecting released, soluble tails, such as by solid-phase affinity adsorption assay. Any convenient method may be used for selectively detecting released tails, which may be detected by an increase in released tails or inferentially as a decrease in bound tails. For example, the tails may provide an affinity tag, such as a native or heterologous epitope (e.g. His tag), biotin or avidin moiety, etc. to facilitate detection by a tag-specific reagent. Alternatively, the tail may be outfitted with a directly or indirectly detectable label, such as with a fluorescer. In particular embodiments, the tail provides a release dependent signal, such as a change in the fluorescent polarization of a labeled specific binding moiety present in the sample. Frequently, selective detection is preceded by separating membrane-bound from released, soluble tails. Any convenient method may be used to separate membrane-bound from released tails, including diffusion, chromotagraphy, centrifugation, solid-phase adsorption, etc.

The recited protease is generally native to the membrane preparation of the sample. LDL receptors are known to be naturally expressed in a wide variety of cell types, and we find that cellular membranes of these cells generally provide assay-usable protease activity. In particular embodiments, the membrane is enriched with the protease, particularly wherein the protease is a membrane-associated, intramembranous or cytosolic protease activity, particularly gamma secretase, e.g. by overexpression or partial purification.

Source materials may comprise membranes prepared from cultured cells or animal or plant tissues, or other prokaryotic or eukaryotic organism such as yeast or bacteria which express the requisite LDL receptor transmembrane domain and protease.

Frequently, the sample further comprises a candidate agent which modulates the resultant cleavage and/or release, wherein an agent-biased cleavage and/or release is detected. Candidate agents encompass numerous chemical classes, though typically they are organic compounds; preferably small organic compounds and are obtained from a wide variety of sources including libraries of synthetic or natural compounds. A variety of other reagents may also be included in the sample. These include reagents like salts, buffers, neutral proteins, e.g. albumin, detergents, protease inhibitors, antimicrobial agents, etc.

We have confirmed LDR receptor signaling by proteolysis assays using a variety of LDL receptor transmembrane domains, in several alternative constructs and in both cell and membrane extract based systems. Table 1 summarizes exemplary systems demonstrating specifically detectable C-terminal tail release.

TABLE 1

Exemplary LDL receptor transmembrane domain proteolysis signaling systems; g-secretase enrichment is effected by overexpression of recombinant g-secretase as described by Levitan et al., Proc Natl Acad Sci USA 2001 Oct 9;98(21):12186-90.

| LDL receptor transmembrane fusion | Cell or Membrane preparation | Protease |
| --- | --- | --- |
| LRP-Gal4/VP16 | HEK 293 cells | endogenous |
| LRP1b-Gal4/VP16 | HEK 293 cells | endogenous |
| Megalin-Gal4/VP16 | HEK 293 cells | endogenous |
| LRP-(His)6 | HEK 293 cell membrane extract | endogenous |
| LRP1b-native LRP1b tail | HEK 293 cell membrane extract | endogenous |
| LRP-Gal4/VP16 | HEK 293 cells | g-secretase enriched |
| LRP-(His)6 | HEK 293 cell membrane extract | g-secretase enriched |

The subject compositions include systems and kits for the disclosed LDL receptor signaling assays. For in vitro assays, for example, such systems and kits comprise predetermined amounts of a suitable LDL-receptor transmembrane fusion construct. The systems and kits will generally also comprise further reagents described herein to facilitate the proteolysis reaction, suitable packaging, and written instructions describing a disclosed assay protocol.

The following experimental examples section is offered by way of illustration and not by way of limitation.

EXAMPLARY DETAILED EXPERIMENTAL PROCEDURES

Materials: TPA (Phorbol 12-myristate 13-acetate) was purchased from Sigma-Aldrich (St. Louis, Mo.). The compound was solubilized in DMSO at a concentration of 1 mM. For stimulation of transfected 293 cells the cell culture medium (DMEM-low glucose+10% (v/v) FCS+100 U/ml penicillin/100 mg/ml Streptomycin) was exchanged for medium containing 100 nM TPA (+supplements) 30 min to 24 h before cell harvesting.

Plasmids and construction of the LRP-Gal4/VP16 vector: For construction of LRP-Gal4/VP16 the nucleotide 12659–14098 fragment of the LRP-cDNA was amplified by PCR using primers, which introduced Nhe I sites 5'-terminal to the endogenous Hind III site at 12659 and 3'-terminal to the end of the fragment; in addition the stop codon at 14099 was mutated. The PCR product was cloned into the plasmid pMstGV via its NheI sites. pMstGV is based on the commercially available vector pM (Clontech, Palo Alto, Calif.). It codes for a VP16 transactivation domain 3'-terminal to the Gal4 binding domain of pM and no longer carries a stop codon 5'-terminal to the coding sequence for Gal4. The LRP fragment plus the Gal4 and VP16 domains were excised from LRP-pMstGVby Hind III and ligated into the Hind III cut pcDNA3.1-LRP vector. Orientation and sequences of inserts were verified by DNA sequencing. The control plasmid pcDNA3.1-LRP-nonsense contains the described HindIII fragment in the wrong orientation. pMstGV were prepared at UTSW Medical Center, Dallas, Tex., as were the vectors pMstGV-APP695 and pMstGV-LDL-R and the pG5E1B-Luc plasmid, which contains five Gal4 binding sites and the E1B minimal promoter in front of the luciferase firefly gene. pCMV-b-Gal was obtained from Stratagene (La Jolla, Calif.).

Cell Culture and transfection of 293 cells: The human embryonic kidney cell line HEK 293 (CRL-1573, ATCC) was maintained in monolayer culture at 37° C. under a 8% $CO_2$ atmosphere. On day 0 cells were set up at a density of 5×105 per 60 mm dish in Dulbecco's Modified Eagle's Medium (low glucose) containing 100 U/ml penicillin, 100 ug/ml streptomycin sulfate and 10% (v/v) FCS. On day one cells were transfected by calcium phosphate precipitation (MBS Kit™, Stratagene, La Jolla, Calif., used according to manufacturers' instructions) with 9 ug of the pG5 E1B-Luc plasmid, 0.5 ug of pCMV-b-Gal for internal control of transfection efficiency, the respective receptor construct and expression vectors for different adapter proteins or other components as indicated in the text. On day two treatment with TPA or other reagents was started as described above and cells were harvested 24 h to 48 h later.

Reporter gene assays: 293 cells were harvested for reporter gene assays 48 h after transfection. Their culture medium was removed and the cells were washed once with PBS. After addition of 400 ul "Reporter Lysis Buffer" (Promega, Madison, Wis.) per 60mm dish cells were processed according to manufacturers' instructions. Luciferase gene expression was analyzed using the "Luciferase Assay System" (Promega, Madison, Wis.). A 10 s integral measurement of light emission from each reaction mixture was performed in a tube luminometer (Octopump II, MOM Instruments).

β-Gal assays for internal control of transcription efficiency were carried out with an aliquot of the cell lysates prepared for the luciferase assay using the 'Chemiluminescent b-Gal Detection Kit" (Clontech, Palo Alto, Calif.). Normalization of luciferase activity to b-Gal activity was done by dividing RLU values obtained with the first assay by those from the latter reaction. All transfections for reporter gene assays were repeated in at least two independent experiments.

SDS-Page and immunoblot analysis: SDS-Page and immunoblotting were performed according to standard procedures. Briefly, equal amounts of protein as determined with the Coomassie Plus Protein Reagent (Pierce, Rockford, Ill.) were loaded on 4–12% SDS PA gels. After electrophoresis and protein transfer on a PVDF membrane immunoblot, analysis was carried out with rabbit polyclonal antibodies against a C-terminal fragment of LRP. Bound antibodies were visualized with peroxidase-conjugated anti-rabbit IgG by using the SuperSignal CL-HRP Substrate (Pierce, Rockford, Ill.) according to the manufacturer's instructions.

Experimental Strategy. The Gal4/VP16 fusion protein, which consists of the DNA binding domain of the yeast Gal4 transcription factor and of the transactivating domain of the Herpes simplex virus protein VP16, is able to drive transcription from a luciferase reporter plasmid that contains five Gal4 binding elements in front of the adenoviral E1B minimal promoter and the firefly luciferase gene. If the Gal4/VP16 construct is fused to a membrane bound protein, e.g. to the LDL receptor, transcription of the reporter gene is lost, as the Gal4/VP16 domains can no longer translocate to the nucleus, where activation of the reporter plasmid would otherwise take place. However, reporter activation is restored, if Gal4/VP16 is fused to a membrane bound protein that undergoes intramembranous proteolysis, e.g. APP. In this case the protein's cytoplasmic tail carrying the Gal4/VP16 domains is freed and can be transported to the nucleus. This experimental design can be used to test a given membrane protein for intracellular or intramembranous cleavage, if the Gal4/VP16 chimera is fused to the cytoplasmic tail of the protein under investigation. Cotransfection of such a construct and of the Gal4-luciferase reporter in cultured cell lines will lead to expression of the luciferase gene only if cleavage takes place.

Liberation of LRP's C-Terminus by Intracellular/Intramembranous Cleavage To examine whether LRP can be cleaved intramembranously or intracellularly we constructed an LRP-Gal4/VP16 fusion protein. When this construct was contransfected into 293 cells with the pG5E1B-Luciferase reporter, high enzyme activity could be detected. It was two magnitudes greater than in control cells transfected with the LDL-receptor-Gal4/VP16 construct and than the background of luciferase activity in cells transfected with the reporter gene only. For this demonstration, 293 human embryonic kidney cells were transfected with 1.5 ug pG5E1B-Luciferase and 1 ug receptor-Gal4/VP16 expression plasmid or 1 ug pMstGV respectively. 0.05 ug pCMV-b-Gal were cotransfected for normalization to transfection efficiency. After 48 hours cell lysates were prepared and examined for luciferase and β-glactosidase activity. RLU values were obtained by division of luciferase by b-glactosidase activity.

Intracellular/intramembraneous LRP-Cleavage Is Stimulated by TPA in a Time-Dependent Manner. For this demonstration, 293 cells were transfected with 4.5 ug pcDNA3.1-LRP-Gal4/VP16, 4.5 ug pG5E1B-Luc and 0.25 ug pCMV-b-Gal. After 48 h corrected luciferase activity in unstimulated cells was compared to activity in cells stimulated with 100 nM TPA, and revealed a linear increase over the time periods of 12, 16, 20 and 24.

The Stimulatory Effect of TPA Is Specific for LRP-Cleavage. For this demonstration, 293 cells were transfected with 4.5 ug Gal4/VP16-receptor plasmid DNA, 4.5 ug pG5E1B-Luc and 0.25 ug pCMV-b-Gal. 24 h after transfection cells were stimulated with 100 nM TPA for 24 h and then harvested for luciferase activity measurement. The pMstGV-LDL-R construct provided negligible activity under stimulated and unstimulated conditions, a pMstGV-APP construct provided equivalent elevated activity under both stimulated and unstimulated conditions, and the pcDNA3.1-LRP-Gal4/VP 16 provided low activity under unstimulated conditions and greatly elevated (up to 10-fold) activity under stimulated conditions.

TPA Stimulation of 293 and MEF-1 Cells Lowers Endogenous LRP Levels. For this demonstration, untransfected 293 human embryonic kidney cells and MEF-1 mouse embryonic fibroblast cells were stimulated with 100 nM TPA for 24 h or the time period indicated. Then cell lysates were prepared and analyzed by Western Blotting. The antibody used for immunostaining is directed against LRP's C-terminus.

TPA Treatment Leads To Decreased LRP Levels in 293 Cells. For this demonstration, untransfected 293 human embryonic kidney cells and MEF-1 mouse embryonic fibroblast cells were stimulated with 100 nM TPA for various time periods upto 48 h. Then cell lysates were prepared and analyzed by Western Blotting. The antibody used for immunostaining is directed against LRP's C-terminus. Cellular LRP levels were found to decrease by up to approximately 90%, indicating turn-over by proteolytic processing and/or suppression of gene expression.

Decrease of LRP Levels after TPA Treatment is Time-Dependent. For this demonstration, MEF-1 cells were treated with TPA for the time periods of 0.5, 1.5, 5, 5, 6 and 24 h. Then cell lysates were prepared and used for SDS-PAGE and Western Blotting. LRP was stained with an antibody directed against its cytoplasmic tail.

Treatment of 293 Cells with the Proteasome Inhibitor Lactacystin Stabilizes the Intracellular LRP-Cleavage Product. For this demonstration, 293 cells were transfected with 1 ug pcDNA3.1-LRP-Gal/VP16, 1.5 ug pG5E1B-Luc and 0.05 ug pCMV-b-Gal per 60 mm dish. After 24 h cells were treated with 10 or 50 uM lactacystin for 24 h. Subsequently cell lysates were prepared and examined for luciferase activity. β-Gal activity was measured to correct for transfection efficiency. Both 10 and 50 uM treatments provided about 25-fold signal enhancements.

In vitro cleavage of LRP tail. For this demonstration, total cellular membranes from HEK293 cells were prepared by 16,000×g centrifugation of crude cellular homogenate for 20 min after removal of nuclei and mitochondria by sequential centrifugation at 1000×g for 10 min. Membranes were incubated at 0° C. or 37°C. for 1 h before recentrifugation at 100,000×g for 1 hr. Supernatant (S100) and Pellet (P100) fractions were separated by SDS gelelectrophoresis and LRP tail fragment released by proteolytic cleavage from the membranes was detected with a specific antibody. LRP tail fragment was released in the S100 fraction only after incubation at 37° C., not at 0° C.

All publications and patent applications cited in this specification are herein incorporated by reference as if each individual publication or patent application were specifically and individually indicated to be incorporated by reference. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. A method for detecting proteolysis of an LDL (Low Density Lipoprotein) receptor transmembrane domain, comprising the steps of:
   a) providing a sample comprising a cell membrane comprising (i) a polypeptide comprising an LDL receptor transmembrane domain fused to a C-terminal tail, and (ii) a protease which specifically cleaves the domain and thereby releases the tail from the membrane;
   b) incubating the sample under conditions wherein the protease cleaves the domain and thereby releases the tail from the membrane; and
   c) detecting a resultant released tail, which indicates proteolysis of the LDL receptor transmembrane domain.

2. A method according to claim 1, wherein the sample comprises a viable cell which comprises the membrane.

3. A method according to claim 1, wherein the sample comprises a viable cell which comprises the membrane, the tail comprises an intracellular transcription factor domain, the cell further comprises a transcriptional reporter responsive to release of the transcription factor domain from the membrane, and the detecting step comprises detecting expression of the reporter as an indication of the released tail.

4. A method according to claim 1, wherein the sample comprises a cellular membrane extract which comprises the membrane.

5. A method according to claim 1, wherein the sample comprises a cellular membrane extract which comprises the membrane, and the detecting step comprises selectively detecting released, soluble tails.

6. A method according to claim 1, wherein the sample comprises a cellular membrane extract which comprises the membrane, and the detecting step comprises selectively detecting released, soluble tails by solid-phase affinity adsorption assay.

7. A method according to claim 1, wherein the tail comprises an affinity tag.

8. A method according to claim 1, wherein the tail comprises at least a portion of the cytoplasmic domain of the LDL receptor.

9. A method according to claim 1, wherein the protease is native to the membrane.

10. A method according to claim 1, wherein the protease is gamma secretase.

11. A method according to claim 1, wherein the LDL receptor is selected from the group consisting of LRP (LDL Receptor-related Protein), LRP1b (LDL Receptor-related Protein 1b), megalin, LDLR (Low Density Lipoprotein Receptor), VLDLR (very Low Density Lipoprotein Receptor), ApoER2 (Apolipoprotein E Receptor 2), MEGF7 (Multiple Epidermal Growth Factor-like domain protein 7), LRP5 (Low density lipoprotein Receptor-related Protein 5), LRP6 (Low density lipoprotein Receptor-related Protein 5) and LR11 (Low density lipoprotein Receptor 11).

12. A method according to claim 1, wherein the LDL receptor is LRP and the protease is native to the membrane.

13. A method according to claim 3, wherein the LDL receptor is LRP and the protease is native to the membrane.

14. A method according to claim 5, wherein the LDL receptor is LRP and the protease is native to the membrane.

15. A method according to claim 1, wherein the LDL receptor is LRP1b and the protease is native to the membrane.

16. A method according to claim 3, wherein the LDL receptor is LRP1b and the protease is native to the membrane.

17. A method according to claim 5, wherein the LDL receptor is LRP1b and the protease is native to the membrane.

18. A method according to claim 1, wherein the LDL receptor is megalin and the protease is native to the membrane.

19. A method according to claim 3, wherein the LDL receptor is megalin and the protease is native to the membrane.

20. A method according to claim 5, wherein the LDL receptor is megalin and the protease is native to the membrane.

* * * * *